United States Patent [19]

Akiyoshi et al.

[11] Patent Number: 4,870,005
[45] Date of Patent: Sep. 26, 1989

[54] MULTILAYER ANALYSIS ELEMENT

[75] Inventors: Yutaka Akiyoshi; Asaji Kondo; Masao Kitajima, all of Saitama, Japan

[73] Assignee: Fuji Photo Film Co., Ltd., Kanagawa, Japan

[21] Appl. No.: 787,713

[22] Filed: Oct. 16, 1985

Related U.S. Application Data

[63] Continuation of Ser. No. 628,979, Jul. 12, 1984, abandoned, which is a continuation of Ser. No. 440,045, Nov. 8, 1982, abandoned, which is a continuation-in-part of Ser. No. 311,718, Oct. 15, 1981, abandoned.

[30] Foreign Application Priority Data

Oct. 15, 1980 [JP] Japan .................... 55-144849
Oct. 15, 1981 [EP] European Pat. Off. ........ 81108364.1

[51] Int. Cl.$^4$ .................... G01N 31/22; C12Q 1/00
[52] U.S. Cl. ............................ 435/7; 422/55; 422/56; 422/57; 435/805; 436/169; 436/170; 436/810

[58] Field of Search ................. 422/55-57; 436/169, 170, 810; 435/7, 805

[56] References Cited

U.S. PATENT DOCUMENTS

| | | | |
|---|---|---|---|
| 4,144,306 | 3/1979 | Figueras | 422/56 |
| 4,258,001 | 3/1981 | Pierce et al. | 422/56 |
| 4,292,272 | 9/1981 | Kitajima et al. | 422/56 |
| 4,459,358 | 7/1984 | Berke | 436/170 |

Primary Examiner—Barry S. Richman
Assistant Examiner—Jill Johnston
Attorney, Agent, or Firm—Sughrue, Mion, Zinn, Macpeak & Seas

[57] ABSTRACT

A dry type multilayer analysis element comprises at least one porous medium layer comprising a membrane filter, to which an antigen (or antibody) is immobilized, and at least one reagent layer through which a substance(s) which did not participate in an antigen-antibody reaction can permeate.

The multilayer analysis element is effective for assaying components present in body fluids, blood, urine, etc., in a simple manner.

42 Claims, 1 Drawing Sheet

MULTILAYER ANALYSIS ELEMENT

CROSS REFERENCE TO RELATED APPLICATION

This is a continuation application of U.S. Ser. No. 628,979, filed July 12, 1984, now abandoned, which is a continuation of U.S. Ser. No. 440,045, filed Nov. 8, 1982, now abandoned, which is a continuation-in-part of of Ser. No. 311,718, filed Oct. 15, 1981, now abandoned.

1. Field of the Invention

This invention is directed to a multilayer analysis element which enables analysis of a component in a liquid sample, particularly a component present in a body fluid which causes an antigen-antibody reaction.

2. Development of the Invention

To detect an antigen (or antibody) present in a body fluid, particularly in blood, for example, a passive agglutination reaction has widely been utilized in which a testing serum is reacted with animal-originated erythrocyte or latex particles, the surface of which has been sensitized with an antibody (or antigen). If an antigen (or antibody) is present in the testing serum, an antigen-antibody reaction results in causing agglutination; by formation of an agglutinated product, antigen (or antibody) contained in the testing serum is detectable.

However, in a passive agglutination reaction the serum to be tested should be serially diluted and measurement of the titer is performed by a dilution multiple of the limit at which agglutination occurs; this method involves complicated dilution operations and provides merely a semi-quantitative assay.

On the other hand, methods using an antibody (or antigen) labelled with a radioisotope or an enzyme (RIA or EIA) have been utilized. However, these immunoassay methods encounter problems in that they require long periods of time (from about 3 to about 40 hours) for the antigen-antibody reaction, physical separation of a complex formed based on an antigen-antibody reaction from the unbound antigen (or antibody) is necessary, and these methods involve many operational steps.

Multilayer analysis elements for analyzing a component in body fluids are known and as prior art relating thereto, there are, for example, Japanese Patent Publications Nos. 21677/78, 13719/78, 40191/76, 3488/77, 89796/78, 131089/78, etc. However, these all relate to techniques for the chemical analysis of components in blood.

Further, techniques for analyzing components which participate in an immune reaction in blood are disclosed in Japanese Patent Application OPI (the term "OPI" is short for open to public inspection and refers to an application which is unexamined but published) 90859/80, EPC Publication No. 0013156 and U.S. Pat. No. 4,258,001. The invention. disclosed in this prior art is characterized in that heat stable organo-polymeric particles are bonded to an adhesive comprising an organic polymer different from the polymeric particles at their points of contact and the thus prepared three dimensional lattice structure is employed as a porous layer. However, it is extremely difficult to prepare such a stable structure, and such is also expensive.

Further, U.S. Pat. No. 4,168,146 discloses immunoassay involving a diagnostic test strip made of a porous, capillary-possessing carrier material to which antibodies are covalently bound. This metod utilizes the capillary force of the porous carrier material for permitting antigens to migrate so that a considerably long period of time is required for analysis.

SUMMARY OF THE INVENTION

An object of this invention is to provide a multilayer analysis element which eliminates the foregoing drawbacks and can easily be prepared.

Another object of this invention is to provide a multilayer analysis element which enables one to analyze a component having antigenicity or an antibody present in body fluids, particularly blood, serum, urine, etc., in an extremely short time and in a very simple manner.

As a result of various investigations to achieve the above objects, the inventors have found that the above objects can be attained by a multilayer analysis element having the following structure: at least one porous medium layer in which a substance capable of causing a competitive antigen-antibody reaction (e.g., antibody or antigen) is immobilized and at least one reagent layer, characterized in that the porous medium layer is composed of a member selected from the group consisting of a membrane filter, a textile, a non-woven fabric and a water permeable paper and the reagent layer is permeable to a substance which did not undergo antigen-antibody reaction, e.g., an unreacted labelled antigen or unreacted labelled antibody.

The term "immobilization" as used herein refers to fixation of a substance capable of causing an antigen-antibody reaction (e.g., antibody) through a covalent bond, viz., the substance capable of causing a competitive antigen-antibody reaction is predominantly affixed to the inner walls of the porous medium and when fibers are used, fixation predominantly occurs within the porous medium on the surfaces of the fibers. An important feature of this invention lies in occurrence of the immobilization in the interior of the porous medium layer.

BRIEF DESCRIPTION OF THE DRAWINGS

In FIGS. 1 through 3, the numerals represent:

Figure 1:
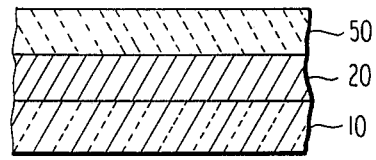
FIG. 1 is a schematic cross sectional view of a multilayer analysis element comprising light permeable support 10 having provided thereon, in order, reagent layer 20 and porous medium layer 50 to which an antibody (or antigen) has been immobilized.

10: light transmitting water impermeable support
20: reagent layer
30: radiation blocking layer
40: adhesive layer
50: porous medium layer
60: spreading layer

PREFERRED EMBODIMENTS OF THE INVENTION

The multilayer analysis element of this invention can have any shape so long as it is suitable for analysis, but a sheet-like or film-like shape is generally preferred.

The multilayer analysis element of this invention can be employed, for example, as described below.

An antigen (or antibody) to be analyzed or quantitatively measured which is contained in a sample is labelled in a conventional manner with a labelling substance and a predetermined or given amount of the labelled substance is mixed with the sample. The mixture is dropped onto a porous medium layer of the multilayer analysis element and reacted with an antibody (or antigen) immobilized in the multilayer analysis element. The antigen (or antibody) in the sample competitively reacts with the antibody (or antigen) immobilized in the multilayer analysis element to form a complex. Excess or unreacted antigen (or antibody) is inherently separated from the complex and diffused into the reagent layer. Unreacted or excess labelled antigen (or antibody) is optically measured as it is or after a color forming reaction with a reagent(s) which are chosen depending upon the labelling substance used; thus the antigen (or antibody) being measured is quantitatively determined.

The multilayer analysis element may comprise a support. In this case, the multilayer analysis element comprises the aforesaid two layers, in the following order going toward the support:

(a) a porous medium layer which can uniformly absorb and spread therein a liquid sample and, at the same time, immobilize an antibody (or antigen) capable of causing an antigen-antibody reaction with an antigen (or antibody) in the liquid sample and permits unreacted antigen (or antibody) to diffuse or transport through pores; and (b) a reagent layer which permits optical measurement of labelled antigen (or antibody) which did not participate in the antigen-antibody reaction in layer (a) described above.

A labelled antigen (or antibody)—the antigen (or antibody) being the same as an antigen (or antibody) in the liquid sample to be analyzed—together with the liquid sample is caused to undergo a competitive antigen-antibody reaction with the antibody (or antigen) immobilized in the porous medium layer (a) mentioned above, unreacted or excess antigen (or antibody) is permitted to diffuse from layer (a) described above into reagent layer (b) and remain in reagent layer (b)—if necessary, being reacted with a reagent(s) additionally incorporated in the reagent layer, depending upon the labelling substance, to form a color.

The multilayer analysis element of this invention can be easily prepared by adhering a porous material of sheet-like or ribbon-like form as a porous medium layer—in which an antibody (or antigen) is immobilized—to a support having coated thereon a reagent layer, or by coating a blushed polymer layer as disclosed in Japanese Patent Publication No. 21677/78 and U.S. Pat. No. 3,992,158 followed by drying, etc.

It is preferred that the porous material possess voids of about 20 to 90%, preferably 50 to 90%, while void percentage varies depending upon the kind of the porous material, pore size, flow rate of a liquid required for analysis, etc.

Porous materials having various pore sizes of about 0.2 to about 20 $\mu$m can be appropriately chosen depending on kind of analyte. For example, in the case that analytes are low molecular weight substances such as insulin, drugs, etc. (these have a molecular weight of from about 400 to 10,000), porous materials having a relatively small pore size are preferably used; if analytes have relatively high molecular weight as in immunogloblins (molecular weight of which is about 160,000) or albumin (molecular weight of which is about 75,000), porous materials having a relatively large pore size are preferably used.

As porous materials described above, membrane filters having various pore sizes—which are known as porous polymer membrane for filtering—textiles (fabrics that are woven or knitted), permeable non-woven fabrics (fibers more closely joined to each other by chemical treatment or heating of fibers per se or fibers adhered to each other using an adhesive) and water permeable paper can be employed.

Typical examples of membrane filters include Microfilter (made by Fuji Photo Film, Co., Ltd.), Millipore (made by Millipore Corporation), etc. These membrane filters generally possesses a pore diameter of about 0.2 to about 20 $\mu$m, preferably 0.3 to 5.0 $\mu$m.

As textiles which can be employed in the porous medium layer, there are a wide variety of textiles; of these textiles, a plain weave which is formed by weaving warp and weft yarns alternately is preferably used. As for the warp and weft which compose such a plain weave, a desirable count ranges from 20 to 120. Among plain-woven textiles, cotton fabrics of the type termed close cloth, canequim, broadcloth and poplin are preferably employed. In addition to other natural fibers woven in the same manners as the above described cotton fabrics (e.g., kapok, flax, hemp, ramie, silk and so on), fabrics obtained by weaving mixed yarns of chemical (e.g., viscose rayon, cuproammonium rayon, cellulose acetate, vinylon, polyethylene terephthalate and so on) and fabrics obtained by weaving chemical fiber yarns in the same manner as in the above described cotton fabrics can also be employed.

The fibers described above can be used in the porous medium layer in the form of permeable non-woven fabrics in a cloth shape.

A wide variety of papers can be employed as paper suited for the porous medium layer so long as they are water permeable; however, paper having a lesser moisture content therein is preferred and paper having relatively long fibers and a thin sheet made of such fibers is also preferred. Particularly preferred is paper which is subjected to an immersion treatment or a compressing treatment is, subjected so as to remove moisture content to as little as possible. A filter paper of thin and fine tissues can be particularly preferably used. A filter paper which is subjected to a compressing treatment is subjected is subjected or which is rendered hydrophilic by immersing the same into a hydrophilic high molecular weight substance solution to thereby reduce the moisture content is particularly preferred. Further, finished paper such as parchment paper, wax paper, etc. can also be employed for the porous medium layer. Indian paper or Japanese paper such as paper made of paper mulberry or Kozo, Mitsumata, etc. are also utilizable. Examples of water permeable paper which can be employed in the porous medium layer of this invention include not only paper made of natural cellulose but also synthetic paper (made of, e.g., polystyrene, polyester, polyethylene, polypropylene, etc.) obtained by paper-making fibers of synthetic high molecular weight substances—which possesses water permeability—, asbestos, glass fiber filter paper, quartz sand made into a paper form, etc.

It is preferred that the porous medium layer have a layer thickness of about 50 μm to about 1 mm; preferably about 50 to about 200 μm when membrane filter is employed, about 100 to 500 μm when textiles or non-woven fabrics are used and, about 200 to about 800 μm when water permeable paper is used.

With regard to the multilayer analysis element of this invention, the structure and materials thereof are more specifically described below.

Figure 2:
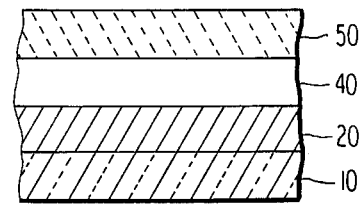
FIG. 2 is a schematic cross sectional view of a multilayer analysis element comprising reagent layer 20 and porous medium layer 50, adhesive layer 40 being provided therebetween.
Figure 3:
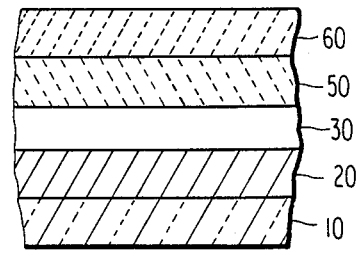
FIG. 3 is a schematic cross sectional view of a multilayer analysis element having a structure such 15 that a light shielding layer 30 is provided between reagent layer 20 and porous medium layer 50 of the multilayer analysis element having the structure shown in FIG. 1 and spreading layer 60—for uniform spreading of an aqueous sample solution—is further provided on porous medium layer 50.

Representative examples of layer structures in specific embodiments of the multilayer analysis elements of this invention are shown in FIGS. 1 through 3.

The multilayer analysis element shown in FIG. 1 comprises support 10 having laminated thereon, in succession farthest from to the support, porous medium layer 50 on which a liquid sample can be spread and which can immobilize therein an antibody (or antigen) capable of causing a specific antigen-antibody reaction with an antigen (or antibody) present in the liquid sample and allows unreacted or excess oxygen (or antibody) to diffuse to reagent layer 20 which permits optical measurement of the unreacted antigen (or antibody) diffused from the aforesaid porous medium layer.

The multilayer analysis element shown in FIG. 2 has a structure where adhesive layer 40 functioning principally to strengthen adhesion force and comprising a hydrophilic high molecular weight substance is provided to adhere reagent layer 20 to the porous medium layer 50.

FIG. 3 is a schematic view of a basic layer structure of a multilayer analysis element of this invention which comprises support 10 having laminated thereon, in succession, reagent layer 20, radiation blocking layer 30, porous medium layer 50 and spreading layer 60. When a drop of an aqueous solution obtained by mixing a liquid sample containing an antigen (or antibody) to be quantitatively analyzed and a known amount of a labelled antigen (or antibody)—which antigen (or antibody) is the same as the foregoing antigen (or antibody)—is spotted on spreading layer 60, the drop is substantially uniformly spread over the spreading layer and then transported into porous medium layer 50. While causing a competitive antigen-antibody reaction with an antibody (or antigen) immobilized in the porous medium layer, the antigen (or antibody) in the liquid sample and the added labelled antigen (or antibody) are competitively reacted therewith to bind with the porous medium layer. Unreacted antigen (or antibody) passes through radiation blocking layer 30 to diffuse into reagent layer 20. Through this process, the antigen-bound antibody is inherently separated from the unbound matters.

In the case that a labelling substance is optically detectable, measurement is optically performed by reflection from the side of support 10; in this case, interference due to the labelling substance bound to the porous medium layer is eliminated by radiation blocking layer 30. In the case that the labelling substance cannot be optically detected as it is, optical measurement can be effected after a color-forming reaction with a reagent(s) contained in the reagent layer. Depending upon the purpose and the accuracy required, analysis can be made with the naked eye, not by optical measurement.

For easier understanding, this invention will be explained in detail, taking as an example the multilayer analysis element having a structure as shown in FIG. 1 and where appropriate, adding an explanation of functional layers additionally provided in the multilayer analysis element as shown in FIG. 2 or 3.

It is necessary that porous medium layer 50 have a great number of pores having a diameter of 0.2 μm or larger, generally 0.2 to 20 μm. In more detail, in order to immobilize, e.g., an antibody and enable binding, e.g., IgG (antibody) having a molecular weight of about 300,000 to about 400,000 and to permit free permeation of an antigen having a molecular weight of from about 200 to about 300,000. It is preferred that the diameter of a pore be larger than 0.2 μm; this lower limit of a pore diameter is also set forth for the reason that a sample liquid, when it is spotted onto the element, is easily permeated into the porous medium layer in a short period of time. On the other hand, in order that a liquid sample be more uniformly spread therein, it is preferred that the diameter of a pore be smaller than 20 μm.

As the porous medium layer, the aforesaid membrane filters, textiles, non-woven fabrics and paper can be employed.

Membrane filters having various pore sizes are commercially available and, depending upon the size of an antigen (or antibody) in a liquid sample, a filter having an appropriate pore size can be chosen.

As examples of processes for rendering fabrics hydrophilic, mention may be made of a process in which commercially produced fabrics are washed and rinsed thoroughly with water to remove starch and other processing materials therefrom and optionally they are further dipped with from 1 to 5% aqueous solutions of surface acrive agents; a process in which surface active agents are incorporated into fabrics in a proportion of 0.1 to 10% per unit weight of fabric by spraying aqueous solutions of surface active agents onto the fabrics to wet them and then drying them:, and so on. Therein, any types of water-soluble surface active agents, namely, nonionic, cationic, anionic and amphoteric agents, can be used. However, nonionic surface active agents such as alkylaryl ethers of polyoxyethylene and polyglycerine, fatty acid esters thereof, sorbitol esters thereof and the like are particularly preferable to other types of surface active agents from the standpoint that the nonionic ones cause hemolysis to much less extent.

In another type of the process for rendering fabrics hydrophilic, fabrics are wet with hydrophilic polymer solutions, which may contain fine powders such as titanium oxide, barium sulfate and the like, and wetting agents such as glycerine, polyethylene glycol and the like, in addition to hydrophilic polymers such as gelatin, polyvinyl alcohol and the like, and then dried. Hydrophilic polymers are incorporated in fabrics in proportion of from about 0.05 to 10% by weight and preferably from about 0.1 to 5% by weight, per unit weight of fabric.

These processes for rendering fabrics hydrophilic can be performed with reference to techniques described in, e.g., U.S. Pat. No. 3,360,448, Japanese Patent Publications Nos. 5332/70, 2603/68 and 2604/68, etc.

A pore size of such porous media can be controlled by a treatment rendering a porous material hydrophilic using a hydrophilic high molecular weight substance aqueous solution containing finely divided powders of titanium oxide, barium sulfate, etc. or wetting agents such as glycerine, polyethylene glycol, etc. By controlling a pore size, a rate of diffusion of unreacted antigen (or antibody) into the reagent layer can be controlled. Such results in good reproducibility.

Immobilization of an antibody (or antigen) in the porous medium layer can be effected using a polyfunctional cross linking agent by chemically linking one of the functional groups of the cross linking agent to a functional group of the porous medium layer and chemically linking the other functional group of the cross linking agent to the antibody (or antigen) in a conventional manner, e.g., as described in *METHODS IN ENZYMOLOGY* edited by K. Mososhack, vol. 44, subtitled "Immobilization of Enzyme", published by Academic Press (1976), S. J. Gutcho, *IMMOBILIZED ENZYMES*, subtitled "Preparation And Engineering Techniques", published by Noyesdata Co., Ltd. (1974), and *KOTEIKA KOSO* (Immobilized Enzyme), published by Kodansha Publishing Co., Ltd. (1975), pages 10-44, which are hereby incorporated by reference. In more detail, various conventional methods are applicable to immobilization of an antibody (or antigen) in the porous medium layer; for example, a glutaraldehyde cross linking method as described in Avrameas et al., *Immunochemistry*, vol. 8, pages 1175-1179 (1971), a maleimide cross linking method as described in T. Kitagawa et al., *J. Biochem.*, vol. 79, pages 233-236 (1976), an isocyanate cross linking method as described in D. Clyne et al., *J. Histochem. Cytochem.*, vol. 21, pages 233-240 (1973), etc.

For example, in the case where the porous medium layer contains a polysaccharide such as cellulose, etc., cyanogen halides or cyanuric halides can be employed as the polyfunctional cross linking agent. In the case that a carboxy group is present in materials of the porous medium layer, water soluble carbodiimides, isoxazolium salts, etc. can be employed; in the case that an amino group is present, dialdehydes, diisocyantes dithioisocyantes, imide esters, disulfonyl chlorides, disulfonyl chlorides, halonitrobenzenes, etc. can be employed.

Most materials used for the porous medium layer are membrane filters, textiles, non-woven fabrics and water permeable paper, which are mainly cellulose and derivatives thereof (cellulose diacetate, cellulose triacetate, cetyl methyl cellulose, etc.); thus, cyanogen halides such as cyanogen bromide, cyanogen chloride, cyanogen iodide, cyanuric halides such as cyanuric chloride, cyanuric bromide, etc., are employed as polyfunctional cross linking agents used for immobilizing an antibody (or antigen). Of these polyfunctional cross linking agents, cyanogen bromide and cyanuric chloride are particularly preferred.

Reaction of a membrane filter, a textile, a non-woven fabric or water permeable paper with cyanogen bromide can be performed in accordance with the process as described in *EXPERIMENT AND APPLICATION, AFFINITY CHROMATOGRAPHY*, Ichiro Chihata, Tetsuya Tosa and Yushi Matsuo, pages 37 to 39, published by Kodansha Publishing Co., Ltd. (1976), R. Axen et al., *NATURE*, vol. 214, pages 1302-1304 (1967), etc.

Reaction of cyanuric acid and a membrane filter, a textile, a non-woven fabric or water permeable paper can be performed as follows.

For example, a membrane filter is immersed in a phosphate buffer saline(PBS, pH 7.3) and a solution of cyanuric chloride in N,N-dimethylformamide is added thereto. The mixture is thoroughly stirred and reacted for 1 to 2 hrs. under ice cooling with stirring after adjusting the pH to 7.0.

The membrane filter to which reactivity is imparted with cyanogen bromide or cyanuric chloride as described above is reacted with an antibody (or antigen) to prepare an immobilized membrane. The immobilized membrane is prepared by repeatedly washing the reactive porous membrane with a saline solution, immersing the same in a solution of an antibody (or antigen) to be immobilized diluted with a saline solution at 37° C. for 1 to 2 hrs., washing with a saline solution, immersing in a saline solution containing bovine serum albumin (to minimize nonspecific binding in a final assay), washing with a saline solution and then drying.

To immobilize an antibody (or antigen) in the porous medium layer, a polyvalent amine or an amino acid can be used as a spacer therebetween without directly linking the antibody (or antigen) to the cyanogen bromide or cyanuric chloride linked to the porous medium layer. After reacting cyanogen bromide or cyanuric chloride with the porous medium layer, a 0.1 to 0.5M aqueous polyvalent amine or amino acid solution is reacted with the reaction product. Thereafter, glutaraldehyde is reacted with the resulting product and then an antibody (or antigen) is linked thereto. The reaction is generally carried out at 37° C. for 30 to 90 mins. under normal pressure.

As polyvalent amines, diamines having 6 to 10 carbon atoms, preferably 6 carbon atoms, such as 1,6-diaminohexane, 1,8-diaminooctane, 1,10-diaminodecane, etc. can be employed. Amino acids having 6 to 10 carbon atoms, particularly 6 carbon atoms, are preferably used and are exemplified by glutamine, alginine, lysine, hydroxylysine, etc. Details of methods using such spacers are described in, e.g., P. O'carra et al., *Biochemical Society Trans.*, vol. 1, pages 289-290 (1973).

In the case that a blush polymer layer as disclosed in U.S. Pat. No. 3,992,158 is formed by coating, cyanuric acid is previously reacted with, e.g., cellulose diacetate used as the polymer and then an antibody (or antigen) is linked thereto under reaction conditions as given for the method using a spacer. The cellulose diacetate having the immobilized antibody (or antigen) is then dissolved in a solvent (e.g., acetone, dichloroethane, etc.) and a blush polymer layer is prepared using the solution in accordance with the process as described in Japanese Patent Publication No. 21677/78 and U.S. Pat. No. 3,992,158.

An adhesive layer can be used as a structural auxiliary layer to exhibit the function of improving adhesion between the porous medium layer and the reagent layer, radiation blocking layer or support, etc. As the adhesive layer, hydrophilic high molecular weight substances such as agarose, polyacrylamide, sodium polyacrylate, copolymers containing acrylic acid, etc. are employed.

The porous medium layer is adhered to the adhesive layer by the application of pressure before the hydrophilic polymer of the adhesive layer is dried, or after the hydrophilic polymer is wet with water or an aqueous solution of a surface active agent. The thickness of the adhesive layer generally ranges from about 0.5 to about 15 $\mu$m, preferably from 0.5 to 5 $\mu$m.

The porous medium layer can also be adhered to the reagent layer by the radiation blocking layer by application of pressure after the hydrophilic high molecular weight polymer used in the reagent layer or the radiation blocking layer is wet with water or an aqueous solution of a surface active agent as above described without providing any particular adhesive layer.

Analysis of a component for immune reaction using the multilayer analysis element of this invention is based upon the principle that a labelled and unlabelled antigen (or antibody) is bound to a specific antibody (or antigen) by a competitive reaction and the concentration of unbound labelled antigen (or antibody) is measured.

As labelling methods which make detection of a known amount of an antigen (or antibody) possible, there are methods which rely on optical detection, methods which utilize a radioisotope, methods using magnetic measurement, etc.; of these, the optical method is excellent in that anybody ca handle the simple devices involved. Methods which rely on optical detection are performed by chemically linking a fluorescent substance, a dye or a dye precursor to an antigen (or antibody), or by linking an enzyme to an antigen (or antibody) and then forming a dye or a fluorescent substance by enzyme reaction in the reagent layer.

Labelling of an antigen ( or antibody) with an enzyme can be performed in accordance with the methods described in Eiji Ishikawa, Tadashi Kawai and Kiyoshi Miyai, *ENZYME IMMUNOASSAY,* published by Igaku Shoin (1978), A. Voller et al., *The Enzvme Linked Immunosorbent Assay,* published by Flowing Publications, Guerney, Europe (1977), etc. Fluorescein-labelling can be performed by the methods described in Tadashi Kawai, *SERIES OF CLINICAL TEST TECHNOLOGY,* vol. 4, subtitled "Immunoserological Test", pages 97–102, published by Igaku Shoin (1977) and EPC Publication No. 0013156. Dyes and leuco dyes can be linked to an antigen (or antibody) in a manner similar to that using an enzyme.

As enzymes for labelling, peroxidase, $\beta$-D-galactosidase, glucose-6-phosphate dehydrogenase or the like can be used. Fluorescein isothiocyanate (FITC), tetramethyl rhodamine isothiocyanate (TMRITC), etc., can be used for fluorescence labelling. Dyes for labelling are not overly limited, and any dyes can be employed so long as the dyes are water soluble and have relatively small molecular weight, such dyes are described in *HANDBOOK OF DYES;* in more detail, merocyanine dyes as described in U.S. Pat. Nos. 2,493,748, 2,519,001 and 2,652,330, cyanine dyes as described in U.S. Pat. Nos. 2,238,213, 2,503,776, 2,537,80, 3,196,017 and 3,397,060, German Pat. No. 1,177,482, British Pat. No. 904,332, Japanese Patent Publications No. 14112/65 and 23467/65, etc., can be employed.

Dye precursors can also be used and are not particularly limited, but leuco dyes as are used in pressure sensitive recording materials, heat sensitive recording materials, etc. are generally employed.

The reagent layer usually provided under the porous medium layer contains portions of an interactive immune assay composition for optical detection and exhibits the function of receiving unreacted antigen (or antibody) diffused from the porous medium layer and converting the same into an optically detectable product therein. Thus, in the reagent layer, the labelled antigen (or antibody) which is not linked to the porous medium layer but which has diffused into the reagent layer is optically detected. In the reagent layer, a membrane filter, textiles, non-woven fabrics, paper, etc., as used in the porous medium layer, can be employed and the labelled antigen (or antibody) can be freely diffused therethrough from the porous medium layer. In the reagent layer, a hydrophilic high molecular weight substance can be used as a binder.

Examples of binders which can be employed in this invention include natural hydrophilic high molecular weight substances such as gelatin, agarose, sodium alginate, carboxymethyl cellulose, methyl cellulose, etc.; hydrophilic synthetic high molecular weight substances such as polyacrylamide, polyvinyl alcohol, polyvinylpyrrolidone, sodium polyacrylate, polyhydroxyethyl methacrylate, copolymers containing acrylic acid (e.g., N-butylacrylate-acrylic acid copolymer), copolymers containing maleic acid (e.g., maleic anhydridemethyl vinyl ether copolymer), etc.

In the case that a labelled antigen (or antibody) has a molecular weight of several hundred thousands, e.g., such as IgG, agarose, polyacrylamide, sodium polyacrylate and copolymers containing acrylic acid are particularly preferred.

When fluorescein or a dye is employed as a labelling substance, it is optically detectable in the reagent layer as it is and no particular reagent is required in the reagent layer. Examples of useful dyes are rhodamine, etc.

When a leuco dye, e.g., a leuco dye used for pressure sensitive recording paper or heat sensitive recording paper, is employed as a labelling substance, an acidic substance such as acid clay is dispersed in a binder and the dispersion is coated on a support to form a reagent layer; a leuco dye-labelled antigen (or antibody) which is diffused into the reagent layer forms a color therein, whereby optical measurement is permitted.

In the case that an enzyme is used as a labelling substance, the reagent layer is formed by dispersing enzyme substrate (which is specifcally recognized and attacked by the enzyme) and a reducible dye precursor—which forms a dye as a result of enzyme reaction—or a fluorescent substance precursor—which releases a fluorescent substance by the attack of enzyme in a hydrophilic polymer and then coating the dispersion on a support. When the labelling enzyme is, e.g., peroxidase, the reagent layer can be formed (if desired or necessary in double layer form) by dispersing glucose, glucose oxidase (to generate peroxide from glucose), 4-aminoantipyrine and 1,7-dihydroxynaphthalene (reduced dye precursor which is oxidized in the presence of peroxide and peroxidase) in gelatin, agarose or polyacrylamide, etc., and coating the dispersion on a support. Further, in the case that the labelling enzyme is $\beta$-D-galactosidase, 4-methylumbelliferyl-$\beta$-D-galactopyranoside is dispersed in a hydrophilic polymer and a layer is formed on a support therefrom.

For purposes of improving various efficiencies such as coating efficiency, diffusibility of diffusible compounds, reactivity, preservability, etc., surface active agents, pH controlling agents,. finely divided powders, antioxidants and other additives comprising organic or inorganic compounds can also be incorporated into the reagent layer.

By inserting a radiation blocking layer between the porous medium layer and the reagent layer, participation of the fluorescein-labelled or dye-labelled antigen (or antibody) linked to the porous medium layer in optical measurement can be eliminated.

The radiation blocking layer can also eliminate interference based upon erythrocyte or hemoglobin in the case of using whole blood.

The radiation blocking layer is formed by dispersing finely divided white powder, such as finely divided $TiO_2$ or $BaSO_4$, generally in an amount of 1 to 25 wt %

(based on binder weight) in a hydrophilic high molecular weight binder and forming a layer having a thickness of 1 to 50 μm, preferably 2 to 20 μm.

The radiation blocking layer can also be prepared by dispersing 0.5 to 20 wt % of finely divided carbon black in a hydrophilic high molecular weight binder as above and forming a layer having a thickness of 1 to 50 μm. In this fashion, interference in the case of using a colored labelled antigen (or antibody) linked to the porous medium layer or whole blood can be similarly eliminated.

In the case of using the blush polymer layer (membrane filter layer as disclosed in U.S. Pat. No. 3,992,158 and Japanese Patent Publication No. 21677/78) as the porous medium layer, the blush polymer layer is formed in a similar manner by adding 0.1 to 10 wt % of carbon black to a polymer solution. In this case, interference in the case of using a colored labelled antigen (or antibody) linked to the porous medium layer or whole blood as a liquid sample can be eliminated without providing any radiation blocking layer.

A porous medium layer of a black color can be formed by immersing a porous medium in a dispersion of carbon black in an aqueous solution of a hydrophilic high molecular weight (ca. 20,000 to 100,000) substance such as gelatin, polyvinyl alcohol, etc.; in this case, it is unnecessary to provide a radiation blocking layer. In place of carbon black, finely divided $TiO_2$, $BaSO_4$, etc., can also be employed. Carbon black is generally employed in the range of from 2 to 40 wt % based on the hydrophilic high molecular weight substance.

It is a novel concept to use carbon black for a porous medium layer or a radiation blocking layer for the purpose of radiation blocking.

By the use of a layer dyed with a dye absorbing the excitation light of a fluorescent substance used for labelling or with a dye having the same absorption wavelength as is used for labelling as the radiation blocking layer, interference with the labelled antigen (or antibody) can be similarly eliminated.

Excitation wavelength is inherently determined depending upon the kind of a dye used; if fluorescein is used, its excitation wavelength is about 490 nm.

As the uppermost layer of the multilayer analysis element of this invention, a liquid sample spreading layer 50 (hereafter supply referred to as a spreading layer) can optionally be provided. The spreading layer has the effect of uniformly spreading a liquid sample dropped onto the multilayer analysis element. In the case that the porous medium layer is composed of a membrane filter and whole blood is used as a liquid sample, the spreading layer is particularly effective for uniformly spreading the liquid sample.

As the spreading layer, fabrics which have been rendered hydrophilic are employed. Fabrics which are rendered hydrophilic includes fabrics that have been thoroughly cleaned and rinsed with water to defat followed by drying and fabrics that are, after cleaning and rinsing with water to defat, immersed in a small amount of a surface active agent, a wetting agent, a hydrophilic polymer or a dispersion of finely divided powders of $TiO_2$ or $BaSO_4$ in a hydrophilic polymer. Fabrics which are rendered hydrophilic for use as a spreading layer and details thereof are described in Japanese Patent Application OPI No. 164356/80 and following the description thereof, these are useful in this invention.

The thickness of the spreading layer ranges from about 50 to about 500 μm, preferably about 80 to about 300 μm in the case of using non-fibrous isotropically porous (porous in all directions) materials; in the case of using fabrics after hydrophilicity treatment and drying ranges from about 80 μm to about 1 mm, preferably about 100 to about 400 μm.

Supports used for the multilayer analysis element of this invention are not particularly limited but it is preferred that the supports possess light-transmitting capability and, be water impermeable. Specific examples of light-transmitting and water impermeable supports include plastic films such as polyethylene terephthalate, cellulose esters (cellulose diacetate, cellulose triacetate, cellulose acetate propionate, etc.), polycarbonate, polystyrene, polymethyl methacrylate, etc., or a glass plate. Known transparent supports having a thickness of from about 50 μm to about 2 mm can be used.

As supports for the multilayer analysis element in which an antigen (or antibody) labelled with a fluorescent substance is employed, it is desirable to employ a material which exhibits a low degree of fluorescence emission and is transparent to the excitation wavelength. Examples of preferred supports are polycarbonate, cellulose esters, polystyrene, etc.

In the case that a support is hydrophobic and has poor adhesion to the hydrophilic binder of the reagent layer, known treatments to render the surface of the support hydrophilic (e.g., ultraviolet irradiation, electron irradiation, flame treatment, hydrolysis with an alkali, plasma treatment, glow discharge treatment, etc.), provision of a subbing layer having an appropriate adhesive force to the hydrophilic binders of both the support and the reagent layer on the surface of the support, formation of minute uneven areas (brushing, electrolytic etching, etc.) at the surface of the support to a degree such that light transmittance is not significantly decreased, etc., can be performed.

A liquid sample containing an unknown amount of an antigen (or antibody) to be analyzed and a known amount of a labelled antigen (or antibody) are competitively reacted with an antibody (or antigen) immobilized in the multilayer analysis element; in this case, the labelled antigen (or antibody) can be competitively employed with an unknown amount of the antigen (or antibody) per the following methods.

(1) A liquid sample containing an unknown amount of an antigen (or antibody) is mixed with a known amount of a solution of a labelled antigen (or antibody) and the mixture is applied to the multilayer analysis element.

(2) A liquid sample containing an unknown amount of an antigen (or antibody) and a solution of a labelled antigen (or antibody) are successively applied to the multilayer analysis element.

(3) A labelled antigen (or antibody) is previously adsorbed onto the spreading layer and designed so as to release the same upon the application of a liquid sample.

Analytes which can be quantitatively determined using the multilayer analysis element in accordance with this invention include a wide variety of substances such as peptide hormones such as hypothalamus hormones (e.g., TRH, LH-RH, somatostatin), hypophysis hormones (e.g., growth hormone, ACTH, α-MSH, β-MSH, lipotropin, prolactin, TSH, TSH-β, LH, LH-β, FSH, FSH-β, α-subnit, arginine vasopressin, lysine vasopressin, oxytocin, etc.), calcium metabolism regulating hormones (e.g., insulin, proinsulin, C-peptide, glucagon, etc.),digestive tract hormones (e.g., gastrin, secretin, pancreozymin, cholecystokinin, GIP, enteroglucagon, etc.), hormones acting on blood vessels (e.g., angiotensin I, angiotensin II, bradykinins, etc.), placenta hormones (e.g., human chorionic gonadotropin (hCG), hCG-$\beta$, human chorionic somatomammotropin, human chorionic thyrotropin), non-peptide hormones such as steroids (e.g., cortisol, corticosterone, 11-deoxycortisol, 11-deoxycorticosterone progesterone, 17-hydroxyprogesterone, pregnenolone, aldosterone, testosterone, dihydrotestosterone, estradiol, estriol, estrone, 2-hydroxyestrone, dehydroepiandrosterone, etc.), thyroid hormones (e.g., throxine, 3,5,3'-triiodothyronin 3,3',5'-triiodothyronine, etc.), prostaglandins (e.g., prostaglandin A, E, F, etc.); substances other than hormones such as drugs (e.g., digoxin, digitoxin, morphine, LSD, gentamycin, amphetamine, nicotine, etc.), cyclic nucleotides (e.g., cyclic AMP, cyclic GMP, cyclic IMP, cyclic UMP, etc.), enzymes (e.g., $C_1$ esterase, fructose 1,6-diphosphatase, alkaline phosphatase, dopamine beta hydroxylase, pepsinogen, etc.), virus specific antigens (e.g., hepatitis B virus, murine sarcomaleukemia virus wooly monkey leukemia virus, avian tumor virus, plant virus, avian C-type virus, etc.), tumor antigens (e.g., $\alpha$-fetoprotein, CEA, etc.), blood serum proteins (e.g., thyroxin binding globulin (TBG), IgG, IgM, IgE, IgA, $\alpha_2$-microglobulin, properdin, anti-Rh antibodies, transferrin, aplipoprotein, fibrinogen degradation products, antihaemolytic factor, renin, etc.); rheumatism factor, folic acid, neurophysin, somatomedin B, nerve growth factor, epidermal growth factor, staphylococcal enterotoxin A and B, type A toxin of chlostridium botulinum, myosin, encephalitogenic basic proteins, substance P, serotonin, conjugated cholyl bile acid, HBS-antigen, C-reactive protein, HB, treponema pallidum, leptospira, etc.

Of these analytes, those which particularly preferably apply to the analysis element of this invention are IgG, IgM, IgE, IgA, insulin, HBS-antigen, $\alpha$-fetoprotein, human growth hormone, renin, gastrin, LH, FSH, cortisol, angiotensin, ACTH, C-peptide, CEA, glucagon, aldosterone, C-reactive protein, HB, treponema pallidum and leptospira.

In the case of using the multilayer analysis element of this invention for an immune test of serum, examination can be performed using mere trace amount of a sample, i.e., 10 $\mu$l. Further, the multilayer analysis element is extremely useful for the examination of serious cases or with children since whole blood can be used. In addition, there is no need for B/F separation (separation of a free antigen from an antigen-bound antibody) which is required in conventional analysis and the time required for incubation of an antigenantibody reaction is within 1 hr., which is much shorter than with conventional test. Thus, quantitative assay data can be provided in an extremely short period of time. The multilayer analysis element in accordance with this invention is an epoch-making analytical element for the immune test of serum.

A representative example of the embodiments of the multilayer analysis element of this invention will be shown below.

Multilayer analysis film for immunological examination utilizing enzyme-enhanced cycle using enzyme-labelled antigen:

Reagent layer 20 containing reaction reagents causing a reaction which make fluorophotometry or colorimetry possible by reacting with an enzyme used for labelling an antigen is formed on a light transmitting, water impermeable support (e.g., a polyethylene terephthalate film).

A composition for enzyme analysis was mixed with a hydrophilic polymer binder such as gelatin, agarose, polyacryl amide, etc., and the resulting mixture was coated on reagent layer 20 to form a coating. In the case of labelling with peroxidase, one composition for enzyme analysis comprises glucose, glucose oxidase, 4-aminoantipyrine and 1,7-dihydroxynaphthalene.

Then, a dispersion of 1 to 25 wt % of finely divided $TiO_2$ or $BaSO_4$ in a polyacrylamide solution was coated on the coating formed as above to provide radiation blocking layer 30. Cyanuric chloride is reacted with Microfilter (tradename made by Fuji Photo Film Co., Ltd., cellulose acetates) having a pore diameter of 0.5 to 1.2 $\mu$m and the thus reacted Microfilter is impregnated with a dilution liquid of an antibody to immobilize it in Microfilter. Thereafter, Microfilter is further impregnated with a bovine serum albumin solution. Thus, a stable porous medium layer is prepared. After wetting the film having coated thereon the radiation blocking layer with water, the above described porous medium layer is put on the film followed by pressing.

Further, a cotton fabric is subjected to a hydrophilicity treatment and put on the porous medium layer. B compressing the system, a multilayer analysis element is prepared.

Multilayer analysis film for immunological examination using a fuorescein-labelled antigen:

As a support, a material which does not emit any fluorescein but transmits excitation light is particularly preferred; examples of such materials include polycarbonates, cellulose acetates and polystyrenes.

A reagent layer can be formed by providing an adhesive layer composed of gelatin or polyacrylamide on the surface of the support, putting thereon Microfilter having a pore diameter of from 0.2 to 1.0 $\mu$m and then compressing the whole assembly.

A radiation blocking layer can be formed by coating a dispersion of finely divided white particles of $TiO_2$ or $BaSO_4$ in an aqueous polyacrylamide solution; it can also be formed by coating a dispersion of 0.5 to 20 wt % carbon black.

A porous medium layer and a spreading layer are formed in a similar fashion to the case of using an enzyme-labelled antigen.

This invention will now be described in detail with reference to the examples below, but should not be deemed to be limited thereto.

EXAMPLE 1

Onto a colorless, transparent polycarbonate film (thickness, 180 $\mu$m) which had been subjected to a hydrophilicity treatment by electron radiation, the layers indicated below were coated or laminated in succession in the recited, order to prepare a multilayer analysis element.

| Reagent layer (fluorescein-labelled antibody receiving layer): | |
|---|---|
| Polyacrylamide (average polymerization degree, 18,000; 5% aqueous solution) | 140 g. |
| p-Nonylphenoxyglycerine (25% aqueous solution) | 2 g. |

The above components were homnogeneously mixed and the mixture coated with a small coating machine. The coated layer was dried to form a reagent layer.

Layer thickness of the reagent layer after drying was 8 μm.

| Radiation blocking layer: | |
| --- | --- |
| Water | 50 ml. |
| Finely divided TiO$_2$ particles | 40 g. |
| p-Nonylphenoxyglycerine (25% aqueous solution) | 0.5 g. |

The above mixture was pulverized in a ball mill. Then, a 5% aqueous polyacrylamide solution was added to the mixture followed by mixing. The mixture was coated onto the reagent layer. The thus coated layer was dried to form a radiation blocking layer. Layer thickness of the radiation blocking layer after drying was 8 μm.

Porous material layer:

Microfilter FR-70 (tradename made by Fuji Photo Film Co., Ltd., cellulose diacetate) having an average pore size of 0.7 μm and a thickness of 70 μm was cut into a sheet-like shape and impregnated with 100 ml. of phosphate buffer saline (PBS) (pH 7.3). A solution of 0.5 g. of cyanuric chloride in 2 ml. of N,N-dimethylformamide was added to the Microfilter. While cooling with stirring, the pH of the mixture was adjusted to 7.0 with a 0.5N sodium carbonate solution. The mixture was then reacted for 1 hr. under ice cooling. Thereafter, the reaction mixture was repeatedly washed with a saline solution.

On the other hand, after a saline solution of human IgG was incubated at 63° C. for 10 mins. to modify the human IgG, the human IgG was diluted 100-fold with a saline solution. The Microfilter to which reactivity had been imparted as described above was immersed in the diluted human IgG. Stirring was carried out at 37° C. for 1 hr. to react the modified human IgG with the Microfilter. After completion of the reaction, the Microfilter was washed with a saline solution and immersed in a saline solution containing 0.2% bovine serum albumin at 37° C. for 30 mins. The system was again washed with a saline solution to prepare a porous material layer having immobilized therein the modified human IgG (antigen).

After the surface of the radiation blocking layer was wet with a 0.2% aqueous p-nonylphenoxyglycerine solution, the porous material layer was put thereon followed by compressing. Thus, a porous material layer was formed on the support.

Spreading layer:

Polyester with cotton mixed (mixed spinning ratio, polyester/cotton=75/25) was immersed in an aqueous solution having the following composition to subject the same to a hydrophilicity treatment:

| Polyacrylamide (average polymerization degree, 18,000) (0.8% aqueous solution) | 150 g. |
| --- | --- |
| p-Nonylphenoxyglycerine (25% aqueous solution) | 1 g. |

The surface of the film earlier obtained on which the porous material layer had been provided was wet with a 0.2% aqueous p-nonylphenoxyglycerine solution and then the mixed fabric subjected to the hydrophilicity treatment was put thereon followed by compressing the whole assembly and drying. Thus, a spreading layer was formed to prepare a multilayer analysis film for rheumatoid factor test.

An aqueous sample solution composed of phosphate buffer saline (pH 7.3) and normal rabbit serum in a 1:1 volume ratio was mixed with a 0.001% solution of fluorescent dye FITC-labelled anti-human IgG (made by Medical and Biological Research Laboratories) and unlabelled antihuman IgG (made by Medical and Biological Research Laboratories) as an antibody in various concentrations of from 0 to 0.01%. 10 μl of this aqueous sample solution was dropped onto the multilayer analysis film for rheumaism factor test. The 10 μl sample solution drop uniformly spread in about 15 secs. over the spreading layer and was absorbed therein. This film was incubated at 37° C. for 30 mins. Thereafter, reflection fluorescence intensity was measured from the support side of the film using Fluorophotometer Model 650 made by Hitachi Ltd. Measurement was conducted using an excitation light of 480 nm and an emission light of 520 nm.

From the results shown in Table 1 below, a calibration curve was prepared based upon the change in fluorescence intensity in response to the amount of the unlabelled antibody and mixing of a known amount of the labelled and unlabelled antibodies. Using the calibration curve, an unknown amount of an antibody in a sample solution can be quantitatively determined by measuring fluorescence intensity. Thus, an immune substance in blood can be quantitatively determined rapidly.

TABLE 1

| Concentration of Unlabelled Anti-Human IgG (%) | Intensity of Fluorescence Measured (arbitrary unit) |
| --- | --- |
| 0 | 125 |
| 0.0005 | 400 |
| 0.001 | 530 |
| 0.002 | 690 |
| 0.005 | 880 |
| 0.01 | 970 |
| blank | 53 |

EXAMPLE 2

A multilayer analysis film for rheumatoid factor measurement was prepared using the same materials in the same fashion as in Example 1 except that the following radiation blocking layer was provided in place of the radiation blocking layer of Example 1.

| Radiation Blocking Layer: | |
| --- | --- |
| Polyacrylamide (5% aqueous solution) | 500 g. |
| Carbon black | 2 g. |
| p-Nonylphenoxyglycerine (25% aqueous solution) | 0.5 g. |

The above mixture was coated on the reagent layer followed by drying provided to a radiation blocking layer. Layer thickness of the radiation blocking layer after drying was 8 μm.

After spotting 10 μl of whole blood onto multilayer analysis films obtained in Examples 1 and 2, the films were incubated at 37° C. for 30 mins.

When observation was made from the support surface, patterns of red cells and haemoglobin were slightly seen with the multilayer analysis film of Example 1; however, worth the film of Example 2, such were not seen at all.

EXAMPLE 3

A multilayer analysis element having a structure, as shown in FIG. 1 except that a porous medium layer as described below was laminated on the reagent layer of Example 1 was prepared.

Porous Medium Layer:

After thoroughly washing cotton-mixed polyester (mixed spinning ratio, polyester/cotton=75/25 plain weave) with water and the defatting, the cotton-mixed polyester was immersed in 100 ml. of phosphate buffer saline (PBS) (pH 7.3) and a solution of 0.5 g. of cyanuric chloride in 2 ml. of N,N-dimethylformamide was added thereto. While stiring under ice cooling, the pH of the mixture was adjusted to pH 7.0 using a 0.5N aqueous sodium carbonate solution and the mixture was reacted for 1 hr. Thereafter, the reaction mixture was repeatedly washed with a saline solution.

On the other hand, after a 1% solution of human IgG in a saline solution was incubated at 63° C. for 10 mins. to modify it, the human IgG solution was diluted 100-fold with a saline solution. The mixed fabric to which reactivity had been imparted with cyanuric chloride as described above was immersed in the diluted human IgG solution. Stirring was performed at 37° C. for 1 hr. to react with the modified human IgG. After completion of the reaction, the mixed fabric was washed with a saline solution and then immersed in a saline solution containing 0.2% bovine serum albumin and then washed with a saline solution again. Then, the thus washed mixed fabric was immersed in the following aqueous solution followed by drying:

| | |
|---|---|
| Polyacrylamide (average polymerization degree, 18,000) (5% aqueous solution) | 200 g. |
| Carbon black | 0.5 g. |
| p-Nonylphenoxyglycerine (25% aqueous solution) | 1 g. |

After wetting the reagent layer already obtained with a 0.2% p-nonylphenoxyglycerine aqueous solution, the modified human IgG-immobilized mixed fabric in which carbon black had been incorporated was put on the reagent layer followed by pressing and drying. Thus, a black colored porous medium layer was formed to prepare a multilayer analysis film for rheumatoid facter test.

Onto the multilayer analysis film obtained in Example 3, 10 μl of a sample solution obtained by mixing whole blood and the aforesaid 0.01% FITC-labelled human IgG (9:1 volume) spotted followed by incubation at 37° C. for 30 mins. Using a 9:1 volume mixture of whole blood and diluted buffer PBS as a control, a similar procedure was repeated.

By observation from the support side, no pattern of red cells or the like was noted. Measurement was performed from the support side of this multilayer analysis film using excitation of 480 nm and an emission of 520 nm. Higher fluorescence intensity than per the control was observed.

While the invention has been described in detail and with reference to specific embodiments thereof, it will be apparent to one skilled in the art that various changes and modifications can be made therein without departing from the spirit and scope thereof.

What is claimed is:

1. A multilayer analysis element comprising:
   (A) a spreading layer consisting essentially of a textile;
   (B) a porous medium layer having immobilized therein a substance which causes a competitive antigen-antibody reaction to form a bound antigen-antibody complex; and
   (C) a reagent layer which permeates an unbound free antigen or antibody, wherein the porous medium layer is selected from the group consisting of a membrane filter, woven or knitted fabrics, a nonwoven fabric and a water-permeable paper and is interposed between said spreading layer and said reagent layer and the reagent layer comprises a porous material and, as a binder a hydrophilic high molecular weight substance 2. The multilayer analysis element as claimed in claim 1, wherein the substance which causes a competitive antigen-antibody reaction to form a bound antigen-antibody complex is immobilized in the interior of said porous medium layer.

3. The multilayer analysis element as claimed in claim 1 or 2 wherein said porous medium layer comprises a porous material having a void of from about 20 to about 90%.

4. The multilayer analysis element as claimed in claim 3 wherein said porous medium layer has a thickness of about 50 μm to about 1 mm.

5. The multilayer analysis element as claimed in claim 1 wherein said textile is a plain weave formed by weaving warp and weft yarns alternately.

6. The multilayer analysis element as claimed in claim 1 wherein said porous medium layer has a thickness of about 50 μm to about 1 mm.

7. The multilayer analysis element as claimed in claim 1 wherein said reagent layer has a thickness of 5 to about 200 μm.

8. The. multilayer analysis element as claimed in claim 1 wherein a radiation blocking layer is provided between said porous medium layer and said reagent layer.

9. The multilayer analysis element as claimed in claim 8 wherein said radiation blocking layer is a light reflection or absorption layer and has a thickness of about 1 to about 50 μm.

10. The multilayer analysis element as claimed in claim 8 or 9 wherein said radiation blocking layer comprises a hydrophilic high molecular weight substance containing 0.5 to 20 wt % of carbon black.

11. The multilayer analysis element as claimed in claim 1 wherein 0.1 to 10 wt % of carbon black is contained in said porous medium layer.

12. The multilayer analysis element as claimed in claim 1 wherein said substance causing a competitive antigen-antibody reaction is an antibody or antigen and said substance which did not undergo the antigen-antibody reaction is an unreacted labelled antigen or unreacted labelled antibody.

13. The multilayer analysis element as claimed in claim 1 wherein the hydrophilic high molecular weight substance is a natural hydrophilic high molecular weight substance.

14. The multilayer analysis element as claimed in claim 13, wherein the natural hydrophilic high molecular weight substance is selected from the group consisting of gelatin, agarose, sodium alginate, carboxymethyl, cellulose and methyl cellulose.

15. The multilayer analysis element as claimed in claim 1 wherein the hydrophilic high molecular weight substance is a synthetic hydrophilic high molecular weight substance selected from the group consisting of polyacryl mide, polyvinyl alcohol, polyvinyl pyrrolidone, sodium polyacrylate, poly hydroxyethyl methacrylate, and copolymers containing maleic acid.

16. The multilayer analysis element as claimed in claim 15 wherein the synthetic hydrophilic high molecular weight substance is selected from the group consisting of polyacrylamide, sodium polyacrylate and copolymers containing acrylic acid.

17. The multilayer analysis element as claimed in claim 1, wherein the porous medium is a membrane filter.

18. The multilayer analysis element as claimed in claim 1, wherein the textile of the spreading layer is hydrophilic.

19. The multilayer analysis element as claimed in claim 1, wherein the hydrophilic high molecular substance is polyacrylamide.

20. The multilayer analysis element as claimed in claim 1, further comprising a transparent support which is light-transmitting and which supports in sequence the reagent layer, the porous medium layer and the spreading layer.

21. The multilayer analysis element as claimed in claim 20, wherein the porous medium layer is a membrane filter.

22. The multilayer analysis element as claimed in claim 20, wherein the textile of the spreading layer is hydrophilic.

23. The multilayer analysis element as claimed in claim 20, wherein the hydrophilic high molecular weight substance is polyacrylamide.

24. The multilayer analysis element as claimed in claim 20, wherein the substance which causes a competitive antigen-antibody reaction to form a bound antigen-antibody complex is immobilized in the interior of the porous medium layer 25. The multilayer analysis element as claimed in claim 20, wherein a radiation blocking layer is provided between the porous medium layer and the reagent layer.

26. The multilayer analysis element as claimed in claim 20, wherein the hydrophilic high molecular weight substance is selected from the group consisting of gelatin, agarose, sodium alginate, carboxymethyl cellulose and methyl cellulose 27. The multilayer analysis element as claimed in claim 20, wherein the hydrophilic high molecular weight substance is a synthetic hydrophilic high molecular weight substance selected from the group consisting of polyacrylamide, polyvinyl alcohol, polyvinyl pyrrolidone, sodium polyacrylate, poly hydroxyethyl methacrylate, and copolymers containing maleic acid.

28. The multilayer analysis element as claimed in claim 20, wherein the synthetic hydrophilic high molecular weight substance is selected from the group consisting of polyacrylamide, sodium polyacrylate and polymers containing acrylic acid.

29. An integral multilayer analysis element comprising:
(a) a porous medium layer having immobilized therein a substance which causes a competitive antigen-antibody reaction to form a bound antigen-antibody complex, and (b) a reagent layer which permeates an unbound free antigen or antibody,
wherein said porous medium layer comprises a textile and said reagent layer comprises a hydrophilic high molecular weight substance as a binder.

30. The multilayer analysis element as claimed in claim 29, wherein a transparent support having a light transmitting capability is provided on the back surface opposite the surface on which the porous medium layer is provided.

31. The multilayer analysis element as claimed in claim 29, wherein said textile is a plain weave formed by weaving warp and weft yarns alternately.

32. The multilayer analysis element as claimed in claim 29, wherein the substance which causes a competitive antigen-antibody reaction to form a bound antigen-antibody complex is immobilized in the interior of the porous medium layer.

33. The multilayer analysis element as claimed in claim 29, wherein a radiation blocking layer is provided between the porous medium layer and the reagent layer.

34. The multilayer analysis element as claimed in claim 29, wherein the hydrophilic high molecular weight substance is selected from the group consisting of gelatin, agarose, sodium alginate, carboxymethyl cellulose and methyl cellulose.

35. The multilayer analysis element as claimed in claim 29, wherein the reagent layer is a hydrophilic high molecular weight substance and said hydrophilic high molecular weight substance is a synthetic hydrophilic high molecular weight substance selected from the group consisting of polyacrylamide, polyvinyl alcohol, polyvinyl pyrrolidone, sodium polyacrylate, poly hydroxyethyl methacrylate, and copolymers containing maleic acid.

36. The multilayer analysis element as claimed in claim 31 wherein the reagent layer is a hydrophilic high molecular weight substance and said hydrophilic high molecular weight substance is selected from the group consisting of polyacrylamide, sodium polyacrylate and polymers containing acrylic acid.

37. The multilayer analysis element as claimed in claim 29 wherein the reagent layer is a hydrophilic high molecular weight substance and said hydrophilic high molecular weight substance is polyacrylamide.

38. A multilayer analysis element comprising:
(A) a spreading layer consisting essentially of a textile;
(B) a porous medium layer having immobilized therein a substance which causes a competitive antigen-antibody reaction to form a bound antigen-antibody complex; and
(C) a reagent layer which permeates an unbound free antigen or antibody, wherein the porous medium layer is selected from the group consisting of a membrane filter, woven or knitted fabrics, a nonwoven fabric and a water-permeable paper and is interposed between said spreading layer and said reagent layer and the reagent layer comprises a hydrophilic high molecular weight substance as a binder.

39. The multilayer analysis element as claimed in claim 38, further comprising a transparent support which is light-transmitting and which supports in sequence the reagent layer, the porous medium layer and the spreading layer.

40. The multilayer analysis element as claimed in claim 38, wherein a radiation blocking layer is provided between said porous medium layer and said reagent layer.

41. The multilayer analysis element as claimed in claim 38, wherein the hydrophilic high molecular weight substance is selected from the group consisting of gelatin, agarose, sodium alginate, carboxylmethyl cellulose and methyl cellulose.

42. The multilayer analysis element as claimed in claim 38, wherein the hydrophilic high molecular weight substance is a synthetic hydrophilic high molecular weight substance selected from the group consisting of polyacrylamide, polyvinyl alcohol, polyvinyl pyrrolidone, sodium polyacrylate, poly hydroxyethyl methacrylate, and copolymers containing maleic acid.

* * * * *